US006518050B1

(12) United States Patent
Ambid et al.

(10) Patent No.: US 6,518,050 B1
(45) Date of Patent: Feb. 11, 2003

(54) PROCESS FOR PRODUCING AND EXTRACTING AROMATIC COMPOUNDS

(75) Inventors: Christian Ambid, Tournefeuille (FR); Severine Carle, Toulouse (FR); Gustavo De Billerbeck, Toulouse (FR)

(73) Assignee: Revico (FR)

( * ) Notice: Subject to any disclaimer, the term of this patent is extended or adjusted under 35 U.S.C. 154(b) by 0 days.

(21) Appl. No.: 09/689,828

(22) Filed: Oct. 13, 2000

Related U.S. Application Data

(63) Continuation of application No. PCT/FR99/00909, filed on Apr. 16, 1999.

(30) Foreign Application Priority Data

Apr. 21, 1998 (FR) .............................. 98 04978
Nov. 27, 1998 (FR) .............................. 98 14995

(51) Int. Cl.⁷ .............................. C12P 7/62; C12P 1/00; C12P 7/06; C12P 1/02; G01N 33/569
(52) U.S. Cl. ...................... 435/135; 435/7.31; 435/41; 435/125; 435/126; 435/132; 435/136; 435/146; 435/156; 435/161; 435/163; 435/165; 435/171
(58) Field of Search ................... 435/135, 7.31, 435/41, 125, 126, 132, 136, 146, 156, 161, 163, 165, 171

(56) References Cited

U.S. PATENT DOCUMENTS

| 4,247,541 A | | 1/1981 | Ishida |
| 4,591,559 A | | 5/1986 | Liu et al. |
| 4,656,036 A | | 4/1987 | Wilson et al. |
| 5,215,901 A | * | 6/1993 | Bog et al. .................... 435/125 |
| 5,340,729 A | * | 8/1994 | Krummenacher ........... 435/171 |

FOREIGN PATENT DOCUMENTS

| EP | 0258993 | 3/1988 |
| EP | 0295358 | 12/1988 |
| FR | 1078133 | 11/1954 |
| FR | 2243257 | 4/1975 |
| FR | 2317359 | 2/1977 |
| FR | 2516540 | 5/1983 |
| FR | 2597502 | 10/1987 |
| FR | 2692281 | 12/1993 |
| FR | 2697266 | 4/1994 |
| FR | 2 705 971 | 12/1994 |
| GB | 437121 | 10/1935 |
| GB | 707332 | 4/1954 |
| GB | 712547 | 7/1954 |
| GB | 788335 | 12/1957 |
| GB | 1053789 | 1/1967 |
| GB | 2089836 | 6/1982 |
| JP | 54089081 | 7/1979 |
| JP | 57127495 | 8/1982 |
| JP | 5717695 | 11/1982 |
| JP | 58111659 | 7/1983 |
| JP | 61170380 | 8/1986 |
| JP | 62040259 | 2/1987 |
| JP | 2257832 | 10/1990 |
| SU | 50773071 | 10/1980 |

OTHER PUBLICATIONS

Singleton, P. et al., Dictionary of Microbiology and Molecular Biology, 1991. John Wiley and Sons. p. 374.*

* cited by examiner

*Primary Examiner*—Christopher R. Tate
*Assistant Examiner*—Kailash C. Srivastava
(74) *Attorney, Agent, or Firm*—Hunton & Williams

(57) ABSTRACT

The invention relates to a means for enhancing the value of distillation residues of fermentation products and in particular, a process for producing compounds of economic interest from these distillation residues of fermentation products. This production process also comprises suitable steps for extracting these compounds. In particular, the invention relates to enhancing the value of distillation residues of fermentation products from the agro-feeding industry.

24 Claims, 10 Drawing Sheets

PROCESS FOR PRODUCING AND EXTRACTING AROMATIC COMPOUNDS

This is a continuation of application No. PCT/FR99/00909, filed Apr. 16, 1999.

FIELD OF THE INVENTION

The object of the present invention is means for enhancing the value of distillation residues of fermentation products and in particular, a process for producing compounds of economic interest from these distillation residues of fermentation products. This production process also comprises suitable steps for extracting these compounds.

The invention is particularly concerned with enhancing the value of distillation residues of fermentation products from the agro-feeding industry. Within the scope of the invention, these residues or byproducts are used as substrates for growing microorganisms capable of developing and producing molecules of an economic interest; these compounds are in particular high added value molecules such as fragrances, dyes, enzymes, amino acids, lipids, carbohydrates, biologically active products in the therapeutical, agrofeeding field or for agriculture, etc.

BACKGROUND OF THE INVENTION

FR 2 705 971 describes a process for producing R-γ-decalactone comprising growing microorganisms of the Sporidiobolus or Fusurium genus in a culture medium containing a precursor of R-γ-decalactone selected from ricinoleic acid, lesquerolic acid or salts or esters of these acids with $C_1$–$C_3$ alcohols. Extraction of the produced R-γ-decalactone is performed during the growing process, with an extraction solvent, immiscible with water.

SUMMARY OF THE INVENTION

The inventors within the scope of this invention have observed that residual products from wine distillation, and in particular that of cognac wine (in this specific case, these residual products are referred to by the expression "distilling slops"), are able to form suitable substrates for growing microorganisms, in order to produce molecules of an economic interest.

Accordingly, the object of the present patent application is a process for preparing compounds of an economic interest from substrates comprising or including distillation residues of fermentation products and the use of microorganisms for applying this process. The object of the present application is also a process for extracting the produced compounds, wherein said process is advantageously combined with the production process. Thus, the provided extraction steps according to the invention may follow the production phase(s) of the compounds or be integrated into this phase. If required, conditions selected for the extraction are determined according to their influence on the production of the compounds, for example on the production yield.

Hence, the invention relates to a process for preparing compounds of an economic interest (called "compounds"), comprising the steps of:
 a) growing under aerobic fermentation conditions, at least one microorganism selected for its capability of synthesizing said compounds, in presence of a substrate comprising a residue from the distillation of fermentation products.
 b) recovering the produced compounds.

The object of the invention is in particular a process for producing fragrant volatile compounds (or fragrances).

Advantageously, the invention provides a process which allows natural fragrances to be formed.

For the growing step, fermentation may be carried out in an aerobic, anaerobic or dual medium. The implemented substrate for applying the process comprises for example, a residue from the distillation of fermentation products from plant organs (roots, tubers . . . ) or more generally from plant portions.

DETAILED DESCRIPTION OF THE INVENTION

Figure 1A:
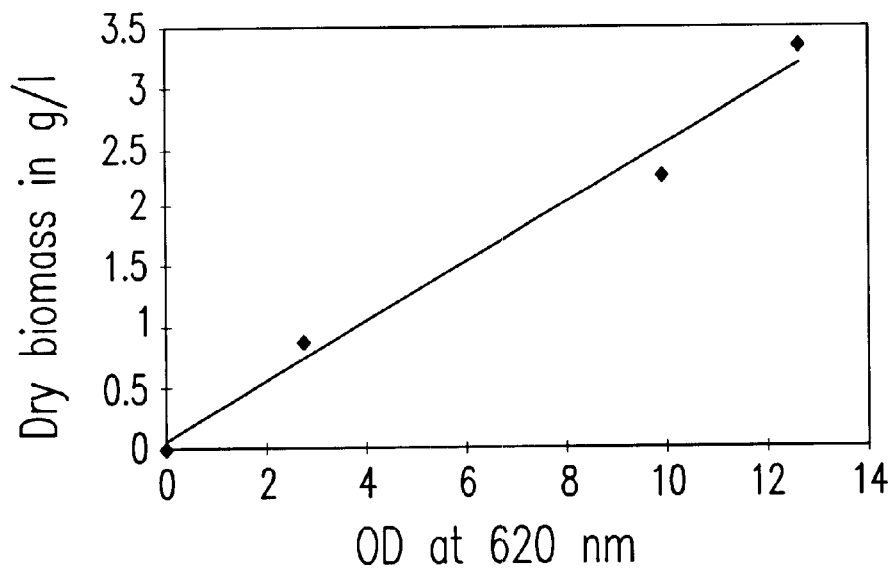
FIG. 1A illustrates the relationship between the biomass and the cellular density.

According to a first embodiment of the process, the implemented substrate comprises a residue from wine distillation and for example, a residue from Cognac or Armagnac wine distillation. This residue is called "distilling slops".

These distilling slops form the liquid byproduct obtained at the exit of a still after wine distillation. Elaboration of cognac is carried out on lees and generates large volumes of distilling slops: about two thirds of the distilled wine volume. The distilling slops no longer contain any alcohol and hardly any aromatic compounds, the latter having passed into the distillate. However they contain a certain number of substances, and especially, significant amounts of organic acids (7.55 to 10.05 g/l).

The average composition of Cognac distilling slops is the following:

| | |
|---|---|
| pH | 3.5 |
| Soluble materials | 1 g/l |
| Dissolved materials | 30 g/l |
| Ashes | 3 g/l |
| COD | 30 g/l |
| $BOD_5$ | 20 g/l |
| Total nitrogen content | 0.5 g/l |
| $P_2O_5$ | 0.6–0.5 g/l |
| $K_2O$ | 2–3 g/l |
| Cl | 0.03 g/l |
| Tartaric acid | 5–6 g/l |
| Succinic acid | 0.5–1 g/l |
| Lactic acid | 2–3 g/l |
| Citric and malic acid | 0.05 g/l |
| Total | 7.55–10.05 g/l |
| Glycerol for normal slops | ca. 7 g/l |

COD is Chemical Oxygen Demand, i.e. the amount of oxygen required for oxidizing the organic materials contained in the effluents.

$BOD_5$ is the Biochemical Oxygen Demand required by microorganisms contained in the water, for 5 days, in order to oxidize part of the carbon materials. Tartaric acid from cognac distilling slops is in the form of potassium bitartrate ($KHC_4H_4O_6$).

Alternatively, according to another embodiment of the invention, the substrate is selected from distillation residues of fermentation products from fruit, beet, cane sugar, cereals, especially malt, barley, wheat, corn or rice.

For example, distillation residues of fermentation products from apple juice are residues from calvados (apple brandy) distillation, distillation residues of fermentation products from cane sugar are residues from rum distillation, etc.

The thus defined substrates, taken individually or as a mixture, may be used for producing different compounds such as fragrant volatile compounds (or fragrances). Other compounds such as proteins, aminoacids, lipids, carbohydrates, nucleosides, alcohols or byproducts from these compounds may be simultaneously produced with these fragrances obtained according to the invention. The described substrates may thus generally enable biologically active compounds to be produced according to the microorganism selected for applying the process.

Substrates defined within the scope of the invention may be adapted for growing various microorganisms and in particular bacteria, yeasts or fungi.

According to a particular embodiment of the invention, the defined process is characterized in that the growing step involves at least a yeast of the *Sporobolomyces odorus* genus capable of producing fragrances, under culture conditions which allow development of said *S. odorus* strain and production of fragrances from a substrate comprising distilling slops.

*Sporobolomyces odorus* is a yeast strain known for its capability of producing fragrances such as lactones, in particular γ-decalactone.

Accordingly the object of the invention is a process for preparing fragrances comprising the steps of a) growing under aerobic fermentation conditions, *Sporobolomyces odorus* in the presence of a substrate comprising distilling slops, wherein the medium's pH is between 4 and 7, preferably equal to about 6, and the reaction temperature is compatible with growth of *S. odorus,* b) recovering the produced fragrances.

The thus defined process is advantageously conducted with stirring between 50 and 1000 rpm, preferably between 100 and 700 rpm and with ventilation of 0.10 to 10 vvm, preferably 0.10 to 5 vvm.

The temperature for the growing step may vary according to the strain(s) of the microorganisms used. For *Sporobolomyces odorus*, the culture process is carried out at a temperature between 10 and 50° C., preferably between 20 and 40° C., advantageously close to 24° C.; this temperature is controlled so as to maintain it essentially constant.

Recovery of the produced fragrances may be carried out by solid-liquid extraction continuously.

The obtained products, among which there are fragrances, may be separated and purified by extraction with a solvent, through distillation, through solid-liquid extraction, through gas-liquid extraction coupled to cryocondensation, through supercritical fluids, through membrane methods, in particular perstraction and pervaporation or through chromatographic separation, in particular HPLC, as well as through combinations of these separation techniques.

According to a particular embodiment of the invention, the step for recovering the produced compounds comprises a step whereby the medium formed by the above defined culture process carried out in the aqueous phase, is brought into contact with a lipid phase medium, for a sufficient period of time, so as to allow all or part of the produced compounds to be absorbed into the lipid phase, wherein the lipid phase medium is solid at room temperature.

In this respect, the invention provides use of lipid media comprising or comprising vegetable fats or mixtures of vegetable fats. As examples, hydrogenated coconut oil (HNCH) (Végétaline from Lesieur), TTT (Fluka Chemie AG) made up from a mixture of tripalmitin (40%) tristearin (40%) and triolein (20%) should be mentioned. Generally, a vegetable fat suitable for applying the invention has the property of being odorless, slightly oxidizable, especially in order to prevent a "stale" odor from occurring, and insoluble in ethanol at low temperatures (below 0° C., especially at −20° C.).

The invention has demonstrated that a suitable extraction system is advantageously based on a phase equilibrium between the aqueous phase and the lipid phase, in order to enhance both viability of the micro-organisms and production of compounds, in particular of fragrances.

The produced fragrances are essentially dissolved in the culture medium which is an aqueous phase. Because their partition coefficients are more favorable for a lipid phase, separation of the fragrances from the fermentation medium may be achieved by solid-liquid extraction, using an oil (or a vegetable fat) which is solid at room temperature. The produced fragrances are thus recovered and concentrated in the solid oil in which they have been absorbed. It is also possible to obtain fragrances in an alcoholate, i.e. as a solution in ethanol. To this end, the solid oil containing the fragrant compounds is solubilized in ethanol. The mixture is then advantageously cooled between −5 and −20° C., for example in molten ice, in order to separate the solid oil from the alcoholate which contains the fragrances in solution. The latter may then be distilled in order to purify the fragrant compounds.

The vegetable fat may consist of a mixture of vegetable fats.

The substrate used may be enriched if necessary in order to promote growth of the strains of microorganisms and/or for promoting production of the sought compounds. For example, an enrichment with carbohydrate compounds and especially with glucose will be required. Alternatively or complementarily, the enrichment may take into account all compounds involved in producing fragrances, such as organic or mineral compounds, especially metal compounds, for example zinc, magnesium or manganese compounds.

The process may also comprise the step of implementing, during the growing step, a precursor capable of promoting production of the sought compounds, in particular a precursor used for the bioconversion, by the applied microorganism(s).

Thus, according to the particular embodiment of the invention, the process is characterized in that the growing step for *Sporobolomyces odorus* is carried out in the presence of selected substrates and ricinoleic acid or ricinoleic acid derivatives, for example an ester, assimilable by the microorganism(s). In a particularly interesting case, when the substrate is distilling slops, the selected micro-organism is *S. odorus* and the precursor is an ester of ricinoleic acid such as methyl ricinoleate.

The inventors have observed that by applying the process, a particularly high level of production may be reached for the sought compounds, when the precursor and in particular methyl ricinoleate is incorporated into the culture medium in fractions throughout the growing step.

This fractionation enables the production of the sought compounds present in the aqueous phase to be increased.

If necessary, this fractionation may take into account steps for extracting the produced compounds, intercalated with additions of precursors.

On the other hand, the inventors have noticed that within the scope of applying the process, addition of a precursor and in particular of methyl ricinoleate is advantageously performed at an early stage during the growing step and preferably upon starting the culture process, whereby this addition is advantageously renewed in equal or different amounts, at different subsequent times during the growing step. For example, addition of precursor and in particular of methyl ricinoleate, may be fractionated into four additions, when the culture period is for example about 3 days.

The process of the invention in a particular embodiment, is characterized in that the amount of methyl ricinoleate introduced during each addition is between 0.008% (v/v) and 5% (v/v), preferably between 0,008% (v/v) and 0.2% (v/v), advantageously between 0.03% and 0.10% (v/v), preferably close to 0.03% (v/v) or advantageously close to 0.18% (v/v) when the extraction is achieved with vegetable fats.

The amount of methyl ricinoleate introduced into the culture may be adjusted according to the desired results.

Advantageously, the amount of methyl ricinoleate introduced during each addition is close to 0.07% (v/v) until a total added amount is obtained between 0.1% (v/v) and 5% (v/v), advantageously between 0.03 and 0.7% (v/v) or 0.1% (v/v) and 0.7 (v/v) at the end of the culture process.

In particular, when extraction is performed by means of vegetable fats this amount is close to 5% (v/v) at the end of the culture process.

For cultivating *Sporobolomyces odorus*, the different parameters for applying the process shall be optimized depending on the amount of compounds which one attempts to produce and when these compounds are fragrances such as γ-decalactone, these parameters may be selected so as to produce between 50 mg/l and 1 g/l, for example between 50 mg/l and 700 mg/l, especially between 50 mg/l and 150 mg/l of γ-decalactone in an aqueous phase.

Generally the total amount and the amount of each fraction of added precursor are determined according to their influence on the bioconversion reaction, on the possible toxicity of the produced compounds towards growth of the strain of microorganisms and according to the duration of the growing step.

The process of the invention is thus characterized in that the growing step may be achieved during a variable period of time and in particular it may be conducted for a period between a few hours and several days, for example up to 10 days, especially for a minimum period of 24 hours, in particular for a period between 24 and 72 hours.

Advantageously, in order to optimize the parameters for applying the process, an initial cellular density (OD at 620 nm) of the microorganisms added for carrying out the growing step, between 0.1 and 20, preferably between 0.2 and 15, advantageously between 1 and 15, is used.

Advantageously, the initial optical density of the microorganisms added for carrying out the growing step, is between 5 and 15 or between 5 and 10.

Furthermore, other compounds may be added to the culture medium and in particular, surfactants are advantageously used such as Tween 20® or antifoam agents.

The inventors have observed that production of fragrances and especially of γ-decalactone is enhanced by addition of these surfactants or antifoam agents and that the initial cellular density (initial biomass) influences this enhancement and the availability of the precursor in the aqueous phase causes the production level for γ-decalactone to vary.

Miscellaneous microorganisms are capable of being grown in presence of substrates of the invention and they may notably be selected from the following strains, if necessary after recombination, capable of causing the compounds identified hereafter to be produced:

| Strains | Products |
| --- | --- |
| *Sporobolomyces odorus* | fragrances, dyes, biomass |
| *Yarrowia lipolytica* | fragrances, biomass, polyols |
| *Saccharomyces cerevisiae* | biomass, ergosterol (→vitamin D) |
| *Lenzites betulina* | fragrances |
| Penicillium sp. | analgesics, fragrances |
| Fusarium sp. | antihypertensives |
| *Fusarium monolilifonne* | plant growth factor, fragrances |
| *Cylindrocarpon radicicola* | steroids, fragrances |
| *Lactococcus lactis* | fragrances |
| Aspergillus | enzymes, fragrances |
| Bacillus | enzymes, fragrances |
| *Claviceps purpurea* | alcaloids, fragrances |
| *Streptomyces dimorphogenes* | enzyme inhibitors, fragrances |

As an example, a strain Yarrowia lipolytica is used such as the one appearing in the ATCC catalog under reference 8661. Advantageously, for applying the invention, the substrate used for growing the microorganisms is sterilized by any suitable means, e.g. in an autoclave, before they are cultivated.

If necessary, the substrate may be used without any preliminary sterilization.

Moreover, the step for recovering the formed products may be conducted in any suitable way and in particular, the obtained products may be isolated and purified through extraction with a solvent, through distillation, through solid-liquid extraction, through gas-liquid extraction coupled to cryocondensation, by using supercritical fluids, by membrane process, in particular perstraction and pervaporation or by chromato-graphic separation, in particular HPLC, as well as by any combination of these separation techniques.

Compound recovery may be performed at the end of the growing step or repeatedly, by interrupting the growing step at determined instants of time, for example depending on the produced amount of compounds and notably for taking into account the toxicity of the produced compounds towards the microorganisms of the culture medium. Alternatively, recovery may be performed in situ, notably when the produced compounds may exhibit a certain level of toxicity towards the microorganisms used.

According to whichever instant is selected for carrying out the extraction, the latter may be performed in the same compartment as that of the production, for example in the same tank, or on the contrary both these steps may be spatially separate.

Possibly, the extraction step conducted continuously along with the production of compounds, may influence the yield of the reaction. Accordingly, when a precursor is used, depending on its partition coefficient and on its concentration in the lipid phase, its availability in the aqueous phase may be affected, consequently reducing its use by the microorganism(s).

The extraction may also promote production of the compounds because an extraction step performed continuously or in a determinate way, alternating with the production step, reduces the possible toxic activity of the produced compounds towards the microorganism(s) of the culture medium.

The suggested variants of the step for recovering the produced compounds are a priori applicable regardless of the operating conditions for the growing step required for producing the compounds, in particular regardless of the applied microorganisms, substrates and/or precursors.

According to a preferred embodiment of the invention, extraction of the produced compounds by their absorption in vegetable fat is followed by separation of the compounds, notably the produced fragrances, by means of an alcohol. Advantageously, such a process comprises the steps of:

1) solubilizing the solid lipid medium in 96° ethanol in an amount of 1V/10V,
2) churning the ethanol solution at −20° C. for an hour,
3) separating the alcohol containing the fragrances of the crystallized lipid medium, for example by filtration.

The object of the invention is also the process for extracting fragrances, implemented independently of the step for producing the fragrances. This extraction process comprises bringing the aqueous phase medium containing the fragrances, into contact with a lipid phase medium, for a sufficient period of time so that all or part of the fragrances may be absorbed in the lipid phase, wherein this process is characterized in that the lipid phase medium is a solid medium at room temperature.

The general and specific conditions for applying this process, described in the above pages are applicable within the scope of its implementation regardless of the conditions for producing the fragrances.

The features of the invention are also illustrated in the examples and figures which follow:

Captions of the Figures

FIG. 1A. Relationship between the biomass (expressed as g/l of dry matter) and the cellular density (OD at 620 nm).

Figure 1B:
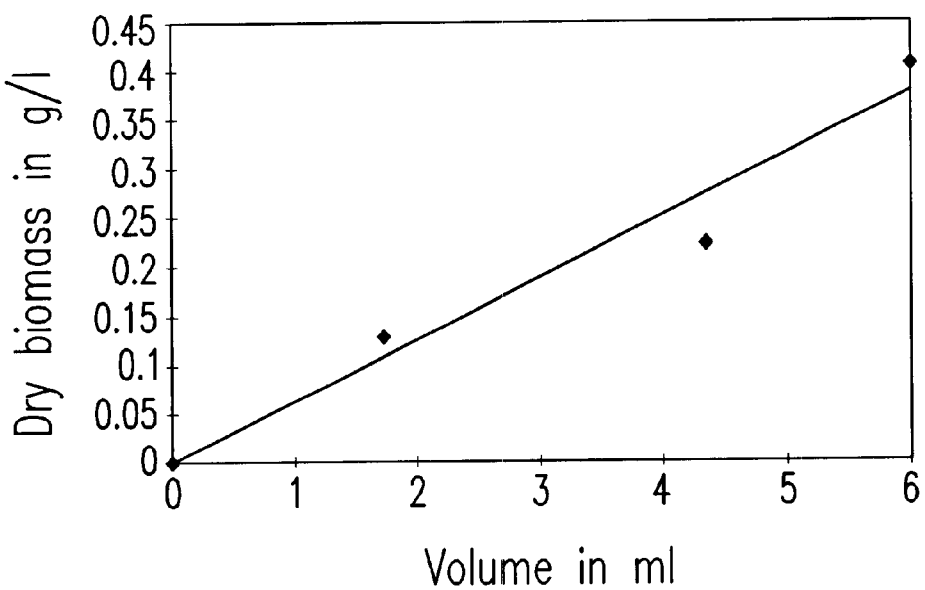
FIG. 1B illustrates the relationship between the biomass and the mycelium volume.

FIG. 1B. Relationship between biomass (expressed as g/l of dry matter) and the mycelium volume.

Figure 2A:
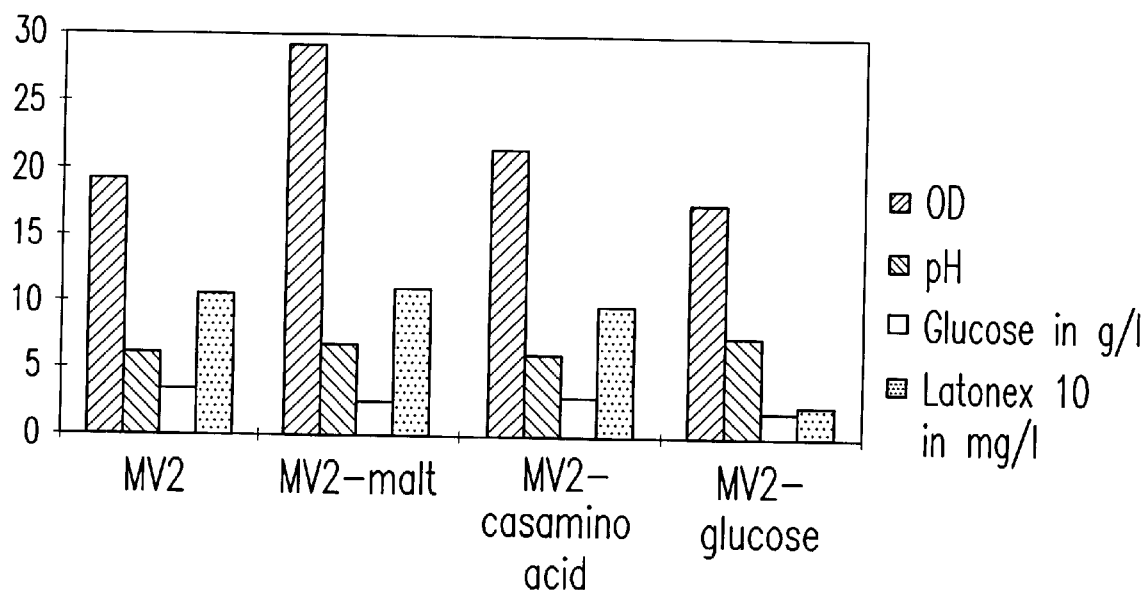
FIG. 2A illustrates the condition of S. odorus cultures of 77 hours of age on different media based on distilling slops.

FIG. 2A. Condition of S. odorus cultures of 77 hours of age on different media based on distilling slops.

Figure 2B:
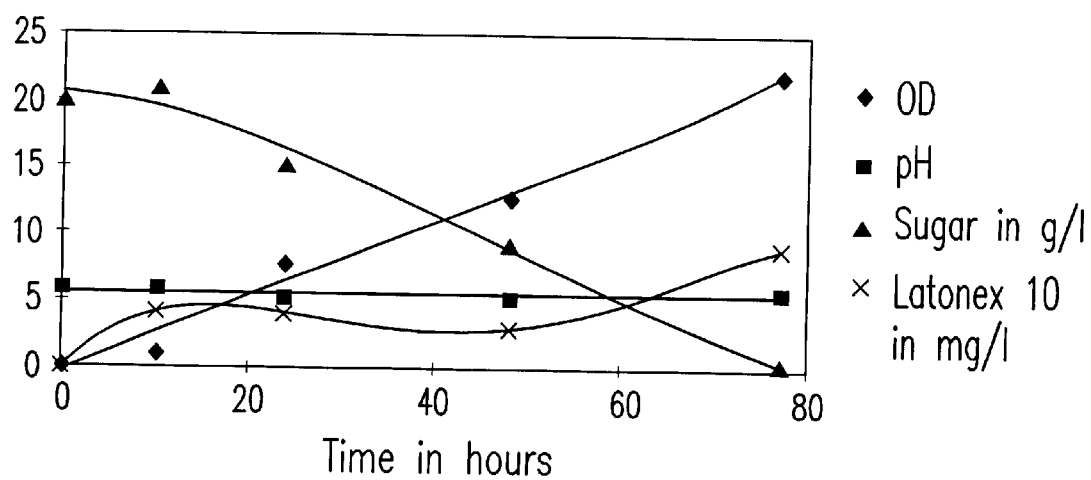
FIG. 2B illustrates the growth and development kinetics of S. odorus on MT2-malt.

FIG. 2B. Growth and development kinetics for S. odorus on MT2-malt.

Figure 2C:
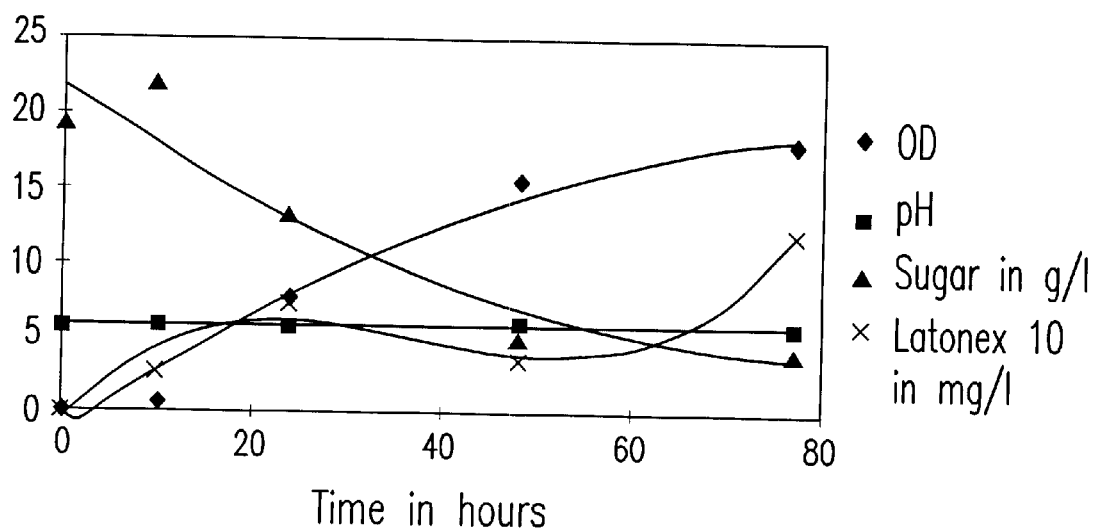
FIG. 2C illustrates the growth and development kinetics of S. odorus on MT2-malt.

FIG. 2C. Growth and development kinetics for S. odorus on MV2-malt.

Figure 3:
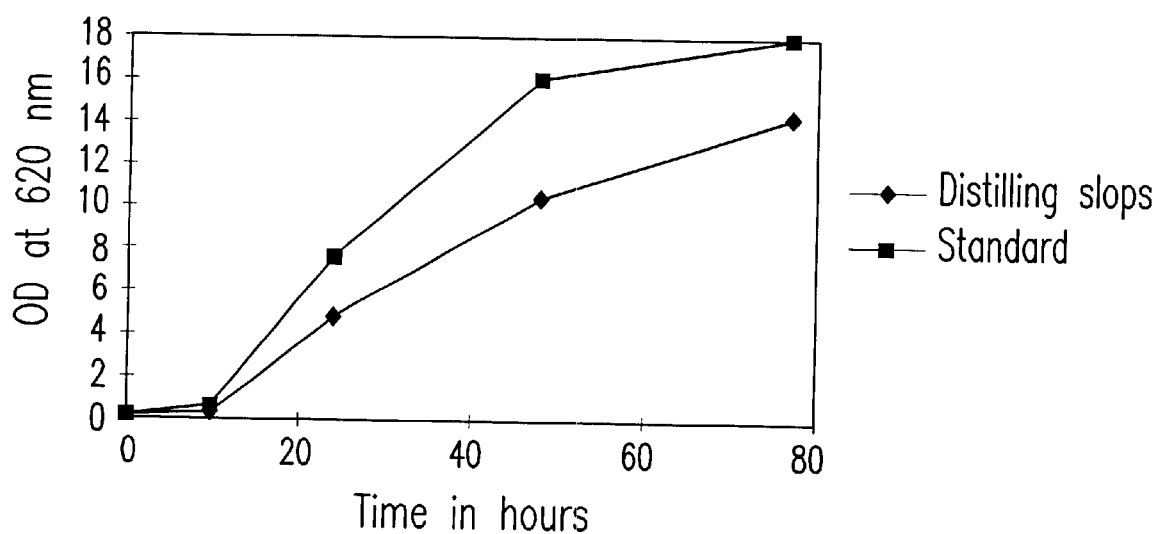
FIG. 3 illustrates the time dependency of biomass production under standard conditions and on non-supplemented distilling slops.

FIG. 3. Time dependency of biomass production under standard conditions and on non-supplemented distilling slops.

Figure 4:
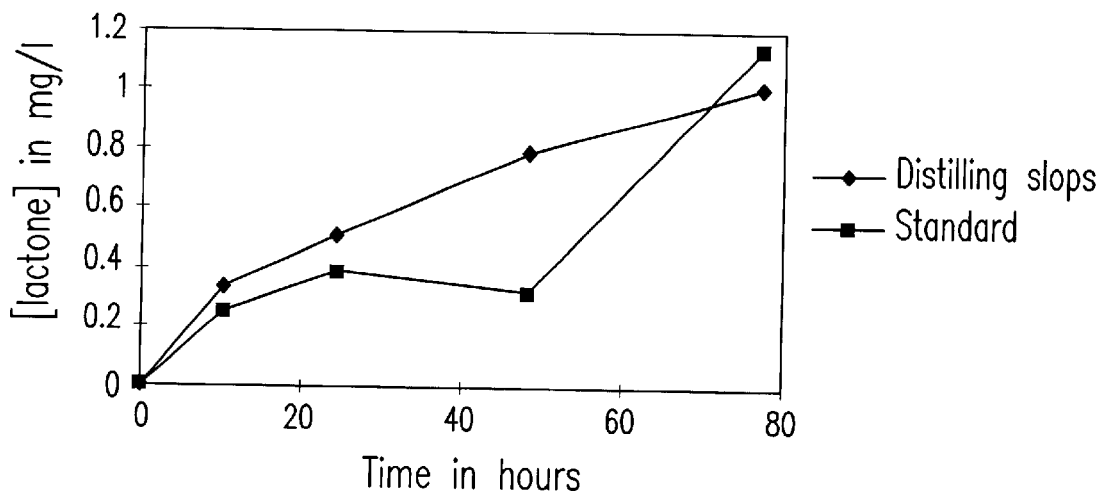
FIG. 4 illustrates the time dependency of lactone production under standard conditions and on non-supplemented distilling slops.

FIG. 4. Time dependency of lactone production under standard conditions and on non-supplemented distilling slops.

Figure 5:
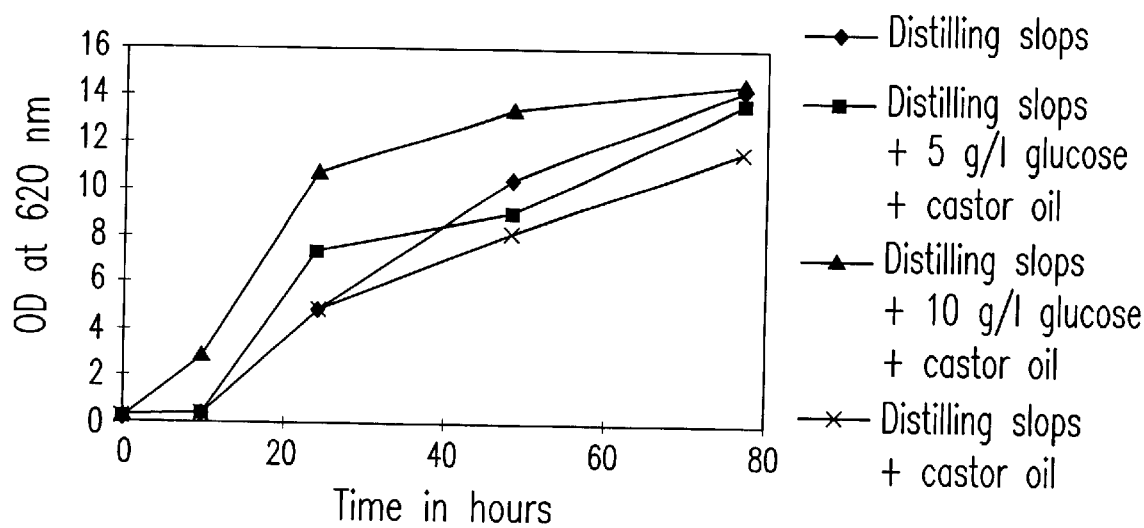
FIG. 5 illustrates the influence of adding 1.66% of castor oil on the time dependency of biomass production.

FIG. 5. Influence of adding 1.66% of castor oil on the time dependency of biomass production.

Figure 6:
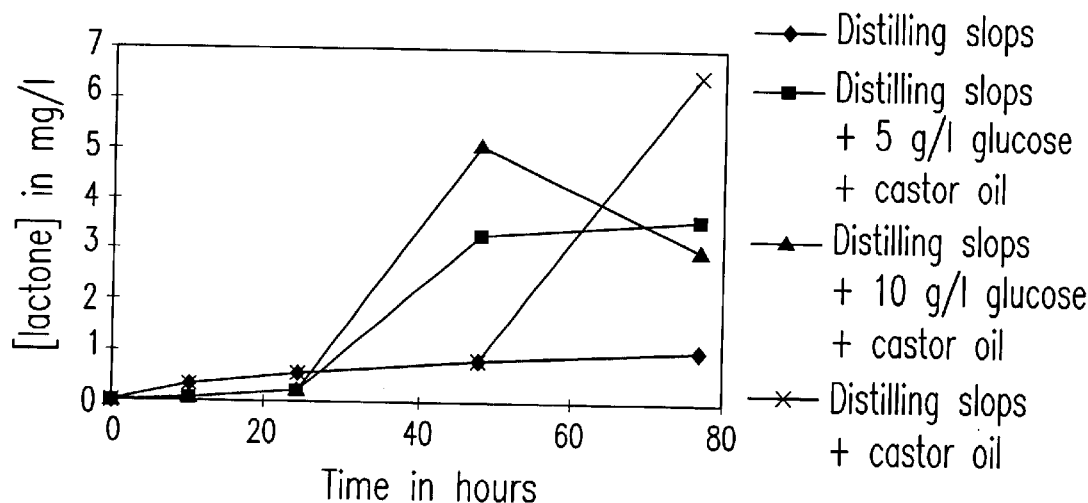
FIG. 6 illustrates the influence of adding 1.66% of castor oil on lactone production.

FIG. 6. Influence of adding 1.66% of castor oil on lactone production.

Figure 7:
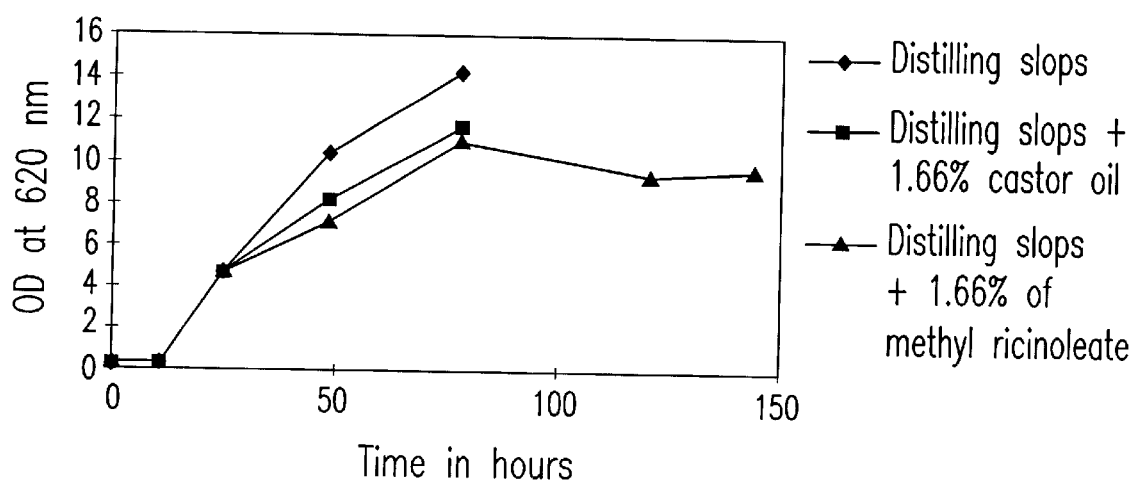
FIG. 7 illustrates the time dependency of lactone production according to the nature of the added lipid compound.

FIG. 7. Time dependency of biomass production according to the nature of the added lipid compound.

Figure 8:
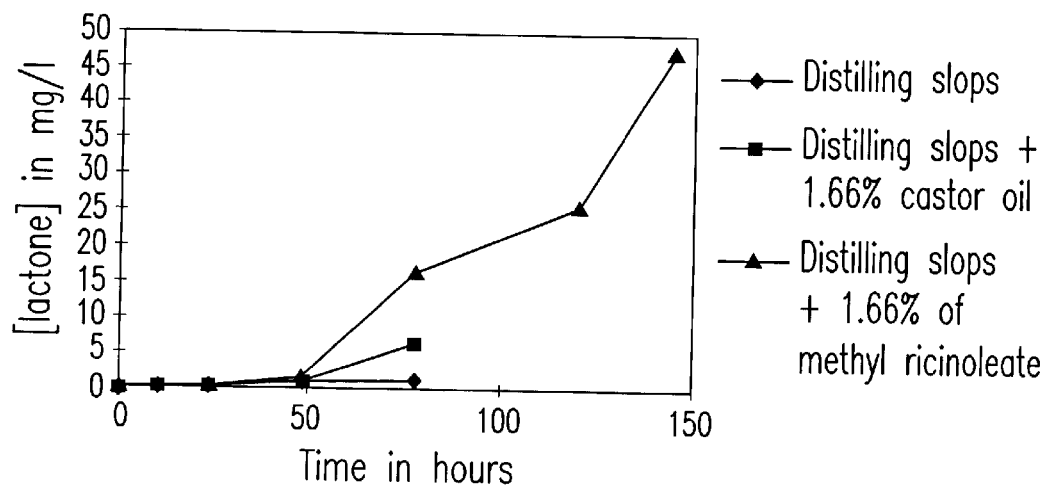
FIG. 8 illustrates the time dependency of lactone production according to the nature of the added lipid compound.

FIG. 8. Time dependency of lactone production according to the nature of the added lipid compound.

Figure 9:
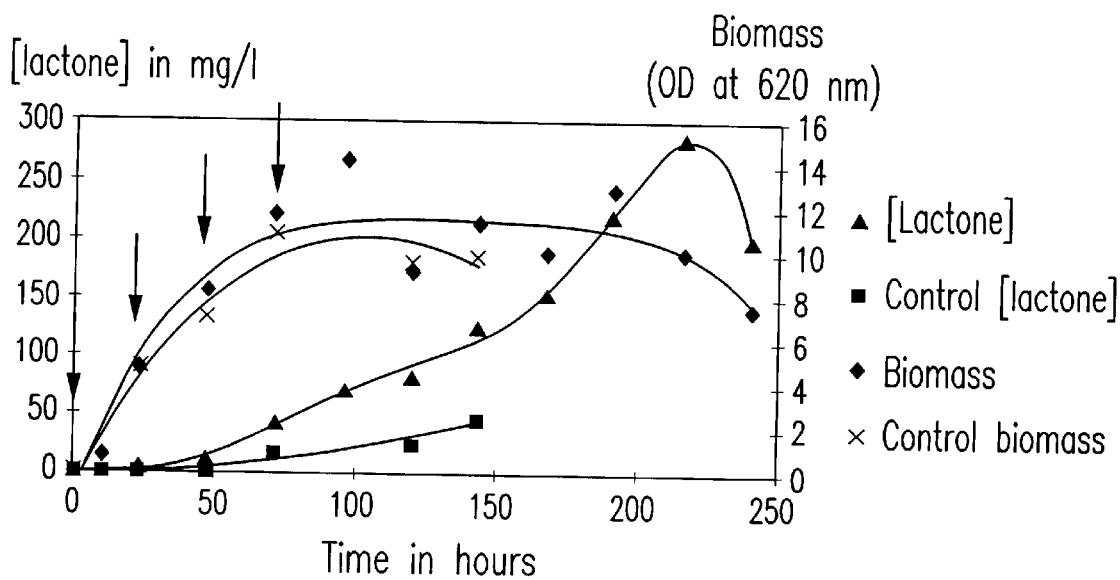
FIG. 9 illustrates the growth and γ-decalactone production kinetics for S. odorus after fractionated additions of methyl ricinoleate.

FIG. 9. Growth and γ-decalactone production kinetics for S. odorus after fractionated additions of methyl ricinoleate. The precursor is added at t=0, 24, 48 and 72 hrs in an amount of 0.06% (v/v). The arrow shows when the precursor was added.

Figure 10:
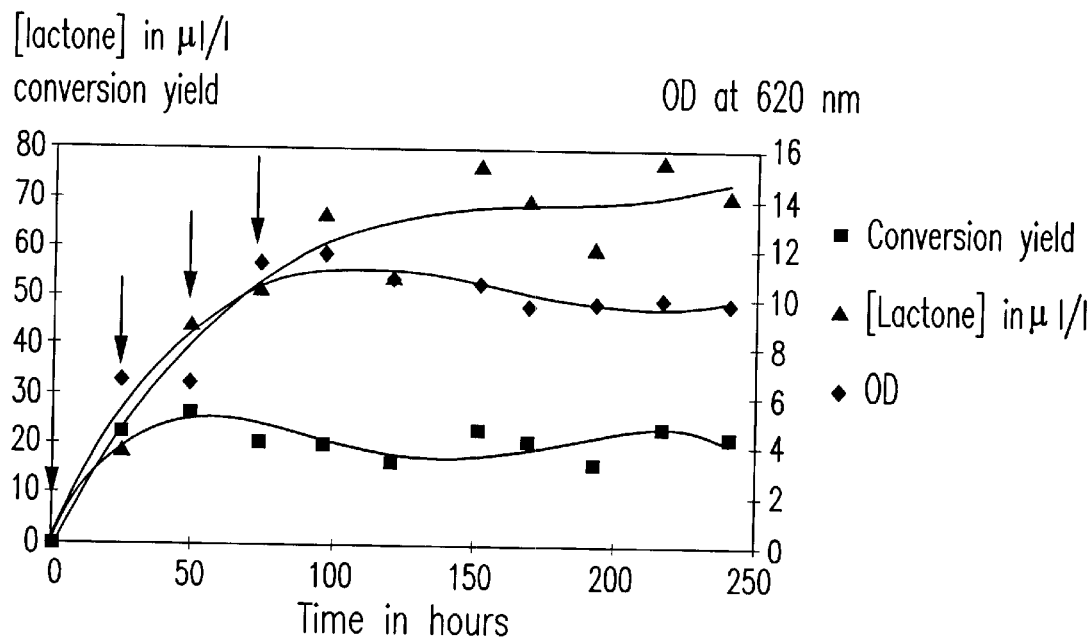
FIG. 10 illustrates the growth, γ-decalactone production and bioconversion yield by cultivated S. odorus after fractionated additions of methyl ricinoleate.

FIG. 10. Growth, γ-decalactone production and bioconversion yield by cultivated S. odorus after fractionated additions of methyl ricinoleate. The precursor is added at t=0, 24, 48 and 72 hrs in an amount of 0.008% (v/v). The arrow shows when the precursor was added.

Figure 11:
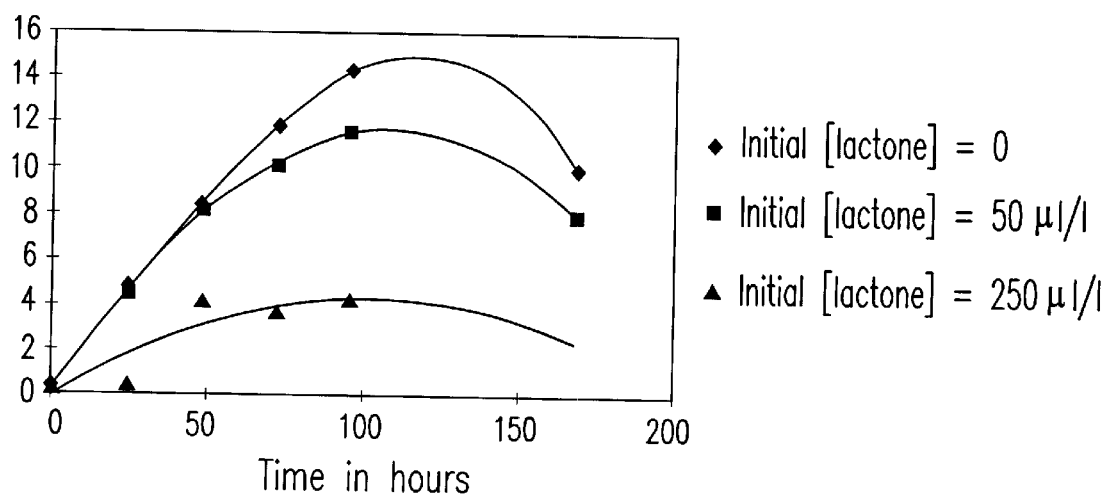
FIG. 11 illustrates the growth of Sporobolomyces odorus versus the amount of γ-decalactone initially present in the medium.

FIG. 11. Growth of Sporobolomyces odorus versus the amount of γ-decalactone initially present in the medium.

Figure 12:
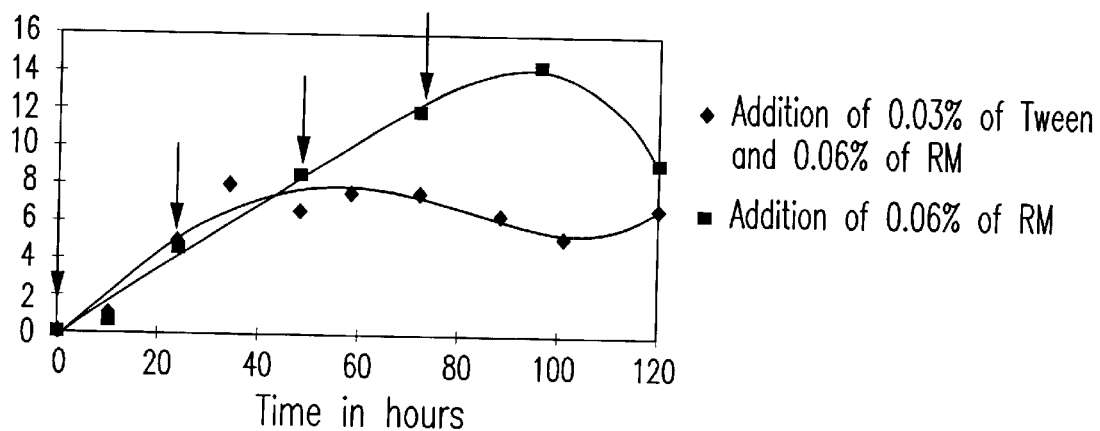
FIG. 12 illustrates the impact of simultaneous addition of Tween 20® and RM on growth of S. odorus.

FIG. 12. Impact of simultaneous addition of Tween 20 and RM on growth of S. odorus. The arrow shows when the precursor was added.

Figure 13:
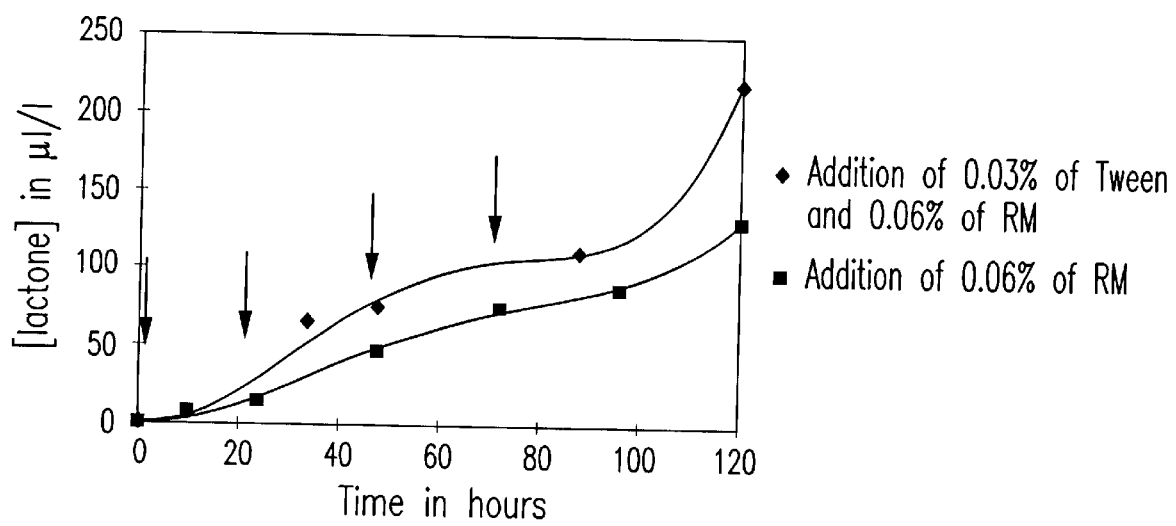
FIG. 13 illustrates the impact of simultaneous addition of Tween 20® and RM on growth of γ-decalactone production.

FIG. 13. Impact of simultaneous addition of Tween 20 and RM on γ-decalactone production. The arrow shows when the precursor was added.

Figure 14:
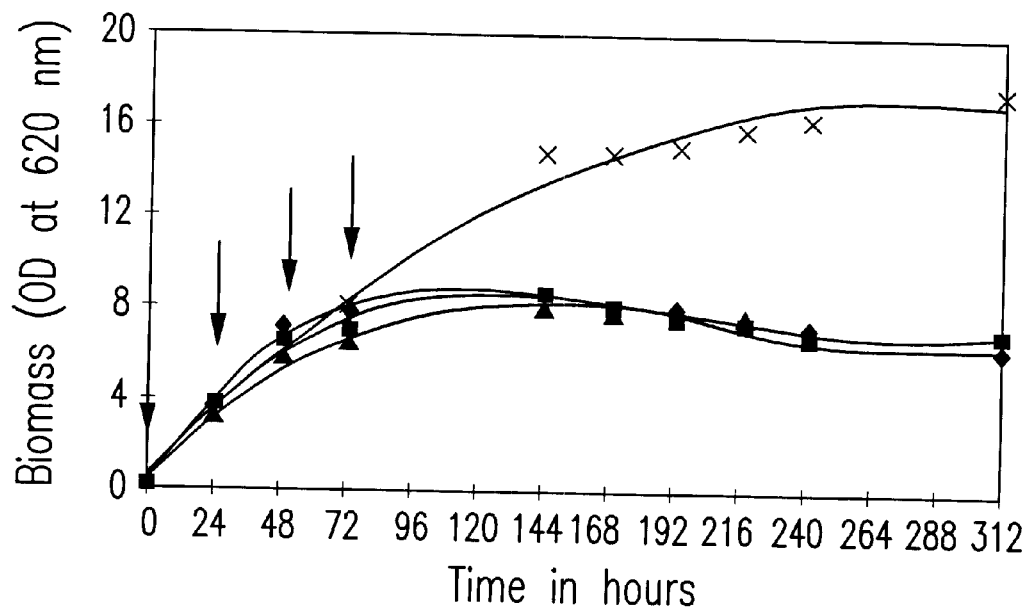
FIG. 14 illustrates the influence of the added quantity of RM on growth kinetics of S. odorus in the presence of HNCH.

FIG. 14. Influence of the added quantity of RM on growth kinetics of S. odorus in the presence of HNCH (5 g/vial).
- ♦ provision of 4×0.003% of RM
- < provision 4×0.06% of RM
- Δ provision of 4×0.12% of RM
- x provision of 4×0.18% of RM
- ↓ shows when RM additions were performed.

Figure 15:
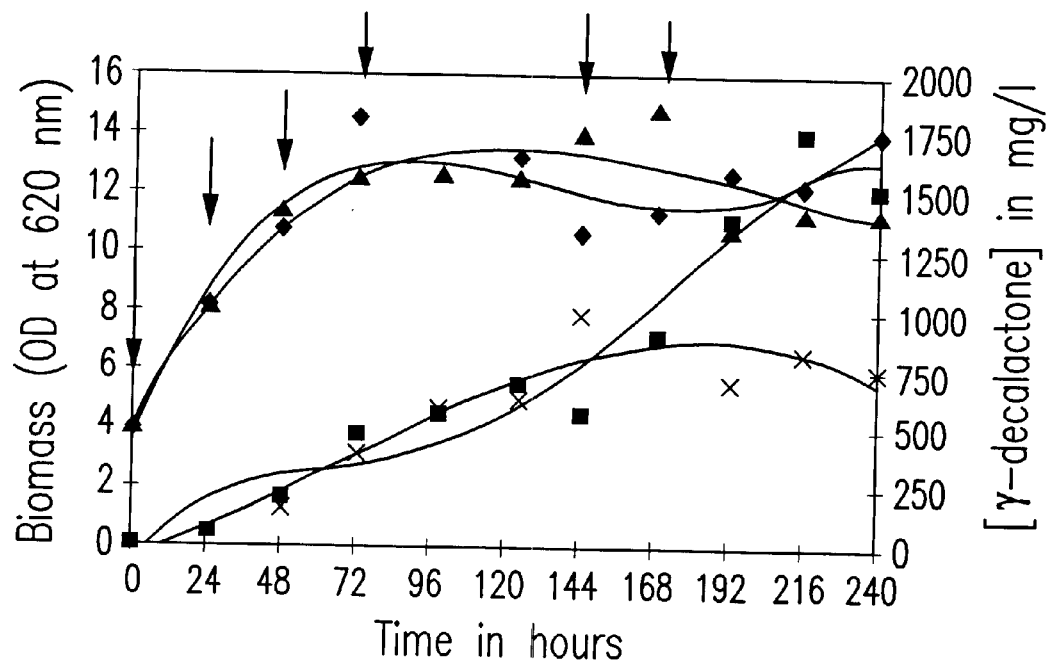
FIG. 15 illustrates the influence of provided supplements of RM, Tween 20® and Struktol® on biomass and γ-decalactone production kinetics for cells of S. odorus sown at an initial density of 4 in the presence of HNCH.

FIG. 15. Influence of provided supplements of RM, Tween 20® and Struktol® on biomass and γ-decalactone production kinetics for cells of S. odorus sown at an initial density of 4 in the presence of HNCH (5 g/vial)
- ♦ 6 provisions of RM: Biomass
- Δ 4 provisions of RM: Biomass
- < 6 provisions of RM: [gama-decalactone]
- x 4 provisions of RM: [gama decalactone]
- ↓ shows when the RM additions where performed.

Figure 16:
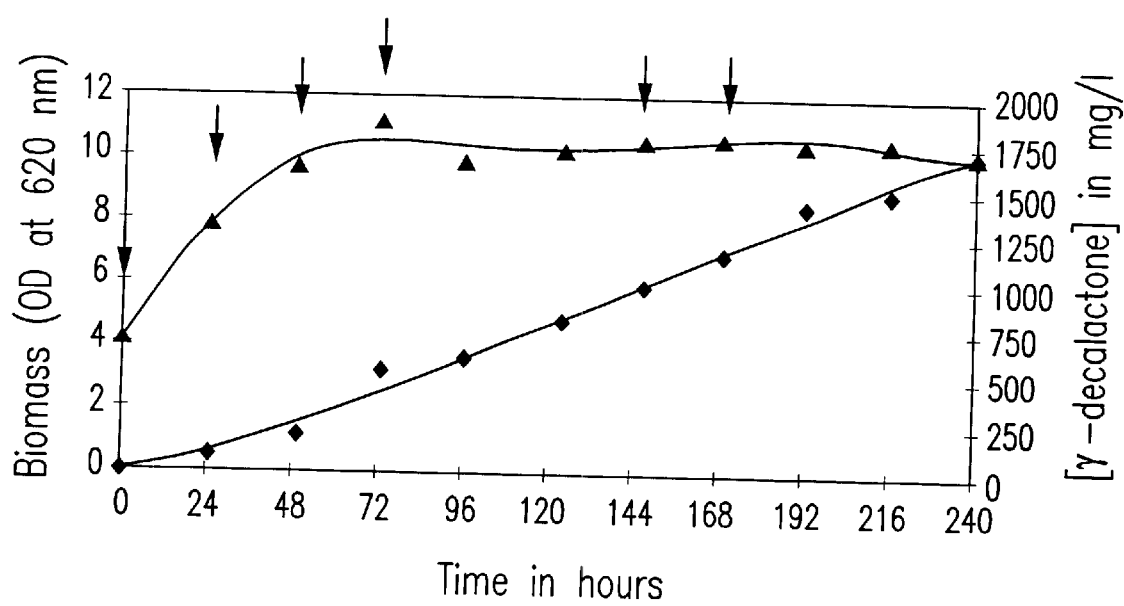
FIG. 16 illustrates the biomass and γ-decalactone production kinetics during growth of S. odorus sown at an initial density of 4 in the presence of TTT.

FIG. 16. Biomass and γ-decalactone production kinetics during growth of S. odorus sown at an initial density of 4 in presence of TTT (5 g/vial).
- Δ Biomass
- ♦ [γ-decalactone]
- ↓ shows when RM additions where performed.

A. Material and Methods

I. STRAINS

I.1—STRAIN OF *SPOROBOLOMYCES ODORUS*

The used *Sporobolomyces odorus* strain is the strain filed under reference CBS 2636.

I.2—STRAIN OF *LENZITES BETULINA* STRAIN

The used strain is the strain filed under reference MIC 38.

II—MEDIA FOR GROWING AND PRESERVING DIFFERENT MICRO-ORGANISMS

II.1—SPOROBOLOMYCES ODORUS

II.1.1—COMPOSITION OF CULTURE MEDIA FOR GROWING *SPOROBOLOMYCES ODORUS*

Two culture media were tested in order to determine the one giving the best γ-decalactone yield. These media may be used as control media for testing the substrates.

The first of these media has the following composition (JOURDAIN, 1985):

- 30 g/l of glucose
- 3.5 g/l of peptone
- 1 g/l of malt extract
- 2 g/l of $KH_2PO_4$
- 0.13 g/l of $CaCl_2$, 2 $H_2O$
- 0.01 g/l de $FeSO_4$, 7 $H_2O$
- 3 g/l of $MgSO_4$, 7 $H_2O$
- $H_2O$ (MT1 medium) or distilling slop, concentrated three times and centrifuged for 5 min at 1000 g (MV1 medium) qsp 1l.

The second medium used (FERON, 1996) is formulated as follows:

- 1 g/l of glucose
- 0.5 g/l of bactotryptone
- 1 g/l of yeast extract
- 1 g/l of malt extract
- 2 g/l of casamino acids
- 2 g/l of $KH_2PO_4$
- 0.13 g/l of $CaCl_2$, 2 $H_2O$
- 0.01 g/l de $FeSO_4$, 7 $H_2O$
- 3 g/l of $MgSO_4$, 7 $H_2O$
- $H_2O$ (MT2 medium) or distilling slops, concentrated three times and centrifuged for 5 min at 1000 g (MV2) qsp 1l.

In both cases, the pH was adjusted to 6 with 5 N caustic soda, then the medium was distributed in 60 ml amounts into 250 ml erlenmeyers and put in an autoclave for 20 minutes at 120° C.

During these culture processes, performed in a liquid medium, temperature was held at 24° C. and stirring was at 250 rpm (revolutions per minute).

II.1.2—COMPOSITION OF THE MEDIUM FOR PRESERVING *SPOROBOLOMYCES ODORUS*

The *Sporobolomyces odorus* strain was kept on a Petri dish at 4° C. In this case, a medium of type MT2 was used. 15 g/l of agarose were added (JOURDAIN 1985). The thus obtained medium was put in an autoclave for 20 minutes at 120° C.

II.2—LENZITES BETULINA

II.2.1—CULTURE MEDIUM FOR *LENZITES BETULINA*

The culture medium used for this basidiomycete fungus has the following composition (GALLOIS, 1990):

- 10 g/l of glucose
- 0.5 g/l of yeast extract
- 0.2 g/l of $KH_2PO_4$
- 0.032 g/l of $CaCl_2$, 2 $H_2O$
- $H_2O$ (LMT) or distilling slops concentrated three times and centrifuged for 5 min at 1000 g (LMV) qsp 1l.

The pH was adjusted to 4.8 with 5 N caustic soda in the case of LMV and with 1N HCl in the case of LMT.

The cultures, grown in a liquid medium in 250 ml erlenmeyers containing 100 ml of medium, were placed at 24° C. with stirring at 180 rpm.

II.2.2—MEDIUM FOR PRESERVING *LENZITES BETULINA*

*Lenzites betulina* was kept at 4° C. on Petri dishes containing a medium prepared in the following way:

- dissolve 39 g/l of potato-dextrose agar, in water
- put the solution of the obtained solution in an autoclave for 20 minutes at 120° C.
- let it cool down to 45–50° C.
- add 14 ml/l of tartaric acid at 10%
- distribute the mixture in Petri dishes.

III—EVALUATION OF THE PRODUCED BIOMASS

III.1—CASE OF *SPOROBOLOMYCES ODORUS*

Time dependency of the amount of biomass produced during cultivation of this yeast, was tracked by measuring the optical density (OD) of the cell suspension at 620 nm. On the spectrophotometer, 0 was obtained with a sample of pure medium (baseline).

Alternatively, measurements of the produced dry material (MS) were performed. For this, 30 ml of a cell suspension were sampled and OD was measured. After centrifugation of this suspension at 2000 g for 5 minutes and removal of the supernatant, the pelet was placed in a drying oven at 37° C. for 48 hours, then it was weighed.

Dry material corresponding to different values of OD was weighed in order to plot the curve MS=f(OD) illustrated in FIG. 1A. The amount of biomass corresponding to a given OD may be determined by the latter curve.

III.2—CASE OF FILAMENTOUS FUNGI

In the case of these fungi, mycelia form "pellets" (bobs) when they are grown in a stirred liquid medium. The produced biom ass was evaluated by measuring the weight of dry material (MS). For this, a sample from the culture having a given volume was centrifuged for 5 minutes at 2000 g in a graduated tube. After this centrifugation, the supernatant was removed, then the volume (V) of the obtain ed mycelium was measured. This pelet was placed in the drying oven at 37° C. for 48 hours and then weighed.

The curve MS=f(V) (FIG. 1B) could be plotted from these measurements. Thus, the amount of corresponding dry biomass could be directly deduced from the volume of obtained mycelia.

IV—DOSAGE OF THE ELEMENTS CONTAINED IN THE CULTURE MEDIA

IV.1—LIQUID-LIQUID EXTRACTION OF VOLATILE COMPOUNDS PRESENT IN THE AQUEOUS PHASE

Before being dosed, the fragrant volatile compounds must be extracted from the medium. For this, the liquid-liquid extraction process was used with an organic solvent, pentane ($C_5H_{12}$). This technique is based on the immiscibility of the solvent with the culture medium which is aqueous and on the higher affinity which aromatic molecules exhibit for it. Thus, free volatile compounds pass from the aqueous phase to the organic phase.

In order to dose the extracted volatile compounds, the so-called internal standard technique was used. This process is based on the use of pentane containing an aromatic compound for performing the extraction. The selected compound should exhibit the following features:

should be added at a known concentration, should not be present in the medium from which the volatile compounds produced by the microorganisms are to be extracted, should have a chromatographic behaviour (retention time, peak area . . . ) close to that of the compounds to be extracted.

In the case of dosages of the lactone produced by *Sporobolomyces odorus*, the internal standard used is geraniol, at a concentration of 30 mg/l.

The followed procedure was as follows:

centrifuge the medium for 5 minutes at 2000 g in order to remove the suspended cells or the "pellets"

fill a 25 ml vial with the supernatant obtained earlier add 1 ml of pentane containing the internal standard, stir for 1 minute so as to bring both phases into contact and to enable the volatile compounds to be extracted from the aqueous phase, let the phases separate out by leaving them for about 30 minutes in ice, sample the organic phase and put it in an Eppendorf tube. For totally destabilizing the emulsion, it might prove necessary to add a drop of absolute ethanol to the mixture.

IV.2—SAMPLE CONCENTRATION

The first dosages of the organic extracts showed that the amounts of the volatile compounds present were not sufficient for obtaining reliable measurements.

To overcome this problem, the samples were concentrated about 5 times. For this, a flux of dry air at a very low flow rate was used. On contacting it, the very volatile solvent evaporated whereas the fragrant molecules were concentrated in the remaining volume. It is believed that either the compounds produced by the microorganisms do not evaporate, or they evaporate in the same proportions as the internal standard.

IV.3—DOSAGE OF THE COMPOUNDS CONTAINED IN THE AQUEOUS PHASE BY GAS CHROMATOGRAPHY (GC)

Equipment

The following chromatograph was used: HEWLETT PACKARD HP 5890 Series II, provided with a capillary column in fused silica impregnated with Carbowax 20M (polymerized polyethylene glycol), of a length of 25 m and a diameter of 0.25 mm.

Chromatograms were made under the conditions described below:

carrier gas: nitrogen with a flow rate of 75 ml/min combustion gas: air/hydrogen mixture temperature—of the injector: 200° C.

of the detector: 250° C.

of the oven→initial: 40° C.

→increase: 4° C./min

→final: 200° C.

The chromatograph was connected to an integrator of the HEWLETT. PACKARD HP 3394A type, used under the following conditions:

attenuation (ATT2A): 0 chart speed (CHT SP): 0,5 cm/min sensitivity (PK WD): 0.04 discrimination (THRSH): 0

Principle for quantifying compounds by the internal standard.

Quantification of the produced compounds was established in the following way: a GPC was carried out from a solution containing 30 $\mu$l/l of internal standard and 30 $\mu$l/l of the compound to be dosed: a lactone in the case of *Sporobolomyces odorus* cultures. From this, the existing ratio between the peak areas of both molecules may be calculated knowing that they are present at the same concentration. Hence, the following is obtained:

Concentration$_{compound\ x}$=(area$_{compound\ x}$/area$_{internal\ standard}$)*response coefficient wherein the response coefficient (CR) has the following value:

CR=30 $\mu$l/l*(area$_{internal\ standard\ at\ 30\ \mu l/l}$/area$_{compound\ x\ at\ 30\ \mu l/l}$)

B. Production of Fragrant Volatile Compounds from Distilling Slops, in the Presence of *S. odorus* and Optionally of Methyl Ricinoleate

1. STUDY OF *SPOROBOLOMYCES ODORUS* BEHAVIOR ON DISTILLING SLOPS

In order to determine whether the distilling slops cause an inhibition on the yeast's growth or bioproduction potential, *S. odorus* was grown on a medium having the same composition as the one used as control (MT), but by replacing water, which served as solvent for the different constituents, with distilling slops concentrated three times and centrifuged beforehand, in order to eliminate the suspended impurities which they contain. After 72 hours of growth, OD was 12 (Table 1), i.e. comparable to that obtained on-medium MT2. These results plus the fact that the presence of γ-decalactone was detected, show that the elements contained in the distilling slops interfere neither with the growth of the yeast, nor with production of lactone.

TABLE 1

*S. odorus* biomass production after 72 hours of cultivation under different conditions

| medium | MT1 | MT2 | MV1 | MV2 | MV1 pH = 3.2 | MV2 pH = 3.2 |
|---|---|---|---|---|---|---|
| OD at 620 nm | 7.0 | 12.6 | 10.0 | 12.0 | 3.2 | 6.6 |
| lactone | +++ | +++ | ++ | ++ | −+ | −+ |

1. Evaluation of the Effect of the pH of the Distilling Slops on the Growth of the Yeast Because the distilling slops have a very acid (about 3.2) and buffered pH, a rather large amount of caustic soda (about 6 g/l) is required in order to bring them back to the optimal pH of the yeast which is 6 (FERON, 1996). It was investigated whether such amounts of caustic soda do not interfere with the yeast's growth and whether the initial pH of the medium based on distilling slops could provide satisfactory growth and production. For this, a culture was produced on an identical medium to the one described above, without any pH adjustment.

Development of *Sporobolomyces odorus* is impaired (OD was 6.6), and above all, production of lactone is very affected (Table 2). From this, it may be stated that a pH of 3 provides neither adequate growth of the yeast, nor maintenance of its lactone production potential as compared with tests carried out on distilling slops at a pH of 6.

2. Search for an Optimum Standard Medium for Growing *Sporobolomyces odorus*

After these first results, the composition of the used medium was optimized in order to determine whether the distilling slops could serve as a substrate for producing lactone. The formulation of the medium was altered by eliminating certain compounds:

distilling slop medium without malt extract
    distilling slop medium without casamino acids
    distilling slop medium without glucose.

After 77 hours of culture, the biomass and γ-decalactone yields were evaluated (FIG. 1A). These measurements reveal that without any malt extract, growth of S. odorus is enhanced.

On the other hand, removal of the casamino acids from the medium does not seem to have any effect on the yeast's development and on lactone production as the obtained results are comparable to those observed on medium MV2.

Finally, suppressing glucose seems to have a negative impact on lactone production, as the latter is considerably reduced.

The medium without any malt may thus be selected as reference medium (MT2-malt) in order to obtain kinetics for growth, production, pH development, glucose and lactone concentration in this medium whether it contains distilling slops or not (FIGS. 2B and 2C).

3. γ-decalactone Production on Non-supplemented Distilling Slops

After demonstrating that all the contained elements in the standard distilling slop medium are not absolutely necessary for growing the yeast and for producing the volatile compounds, its growth and production capacity on non-supplemented distilling slops was evaluated.

For this, growth and production kinetics were obtained on pure distilling slops and after three-fold concentration. The obtained results show that S. odorus is capable of growing and bio-producing under these conditions, i.e. without any carbohydrate addition (FIGS. 3 and 4). After 77 hours, the cultures attain a OD of 14.3. From this OD, it may be stated that the yeast grows satisfactorily, even if OD remains lower than the value obtained under standard conditions, i.e. 18. As for lactone concentration, it reaches 1.14 mg/l under the reference conditions and 1.02 mg/l on non-supplemented distilling slops, respectively. Therefore, it seems that the elements contained in the distilling slops. are sufficient for growing S. odorus and for maintaining its production capacity.

Thus, it seems that no carbohydrate addition is required for producing lactone. These results are in contradiction with the results shown earlier, but they may be explained by the fact there has to be in the supplemented medium, elements capable of limiting use of the organic acids from the distilling slops in the metabolism for synthetizing lactones, either by reacting with them, or by promoting other synthesis routes by their own presence.

4. Use of the Endogenous Potential of Sporobolomyces odorus for Oxidizing Ricinoleic Acid, the Metabolic Intermediate for γ-Decalactone Synthesis In order to improve production of aromatic compounds, we wanted to test the bioconversion route. This strategy is based on the capacity of Sporobolomyces odorus of using ricinoleic acid as a precursor in the metabolism for synthetizing γ-decalactone.

4.1. Impact on Lactone Production from Adding Castor Oil to the Distilling Slops The main source of ricinoleic acid is castor oil wherein it represents about 90% of the fatty acids and it is primarily found in the form of triglycerides.

In order to study the impact from adding castor oil, on the production of γ-decalactone, we produced the following cultures:

distilling slops+1.66% (v/v) of castor oil
    distilling slops+5 g/l of glucose+1.66% (v/v) of castor oil
    distilling slops+10 g/l of glucose+1.66 (v/v) of castor oil.

The obtained results show that adding castor oil to the medium does not interfere with the development of S. odorus as in all cases, the OD reached after 77 hours of culture is close to 14 (FIG. 5).

On the other hand, γ-decalactone production is considerably enhanced: it passes from 1.02 mg/l to 6.47 mg/l, i.e. a 6-fold increase (FIG. 6).

Moreover, production is slightly accelerated in glucose supplemented media but the obtained concentrations remain lower than those obtained without any exogenous glucose (FIG. 6). Accordingly, it seems that an addition of carbohydrates is not required for effective bioconversion of the ricinoleic acid contained in castor oil.

4.2. Effect of Adding Methyl Ricinoleate on γ-Decalactone Production

A second possibility consists in using methyl ricinoleate, i.e., an ester of ricinoleic acid.

In order to test the effect of adding methyl ricinoleate to cultures of S. odorus on distilling slops exclusively, 1 ml of this precursor was added to cellular suspensions of 60 ml of 24 hours of age. By following the latter, it is shown that biomass production is reduced (OD of 11.06 after 77 hours instead of 14.0 on distilling slops, exclusively, FIG. 7), and that of γ-decalactone is considerably enhanced. Indeed, instead of a final concentration, after 77 hours, of 1.02 mg/l on distilling slops or of 6.47 mg/l when castor oil was added, we obtained concentrations of 28.23 mg/l (FIG. 8). This result may be explained by the fact that the lipolytic enzyme which operates in degrading the triglycerides is not synthesized in a constituent way in this yeast. So it would become rapidly a limiting factor in obtaining free ricinoleic acid from castor oil. Adding directly usable methyl ricinoleate overcomes this problem and lactone production yields are improved.

5. Influence of the Time Factor on γ-Decalactone Production

Because of these very interesting results, we attempted to find out whether the obtained concentrations would be increased by letting the cells grow for 144 hours. It turned out that, the medium contained 36.78 mg/l of lactone after 120 hours and 72.24 mg/l after 144 hours. In other words, by increasing the period of time by a factor 1.8, production is multiplied by 2.5. This increase in production coincides with the stopping of cell growth which occurs after a culture period of 72 to 77 hours, and this supports the hypothesis of a decoupling between lactone and biomass productions.

6. Influence of the Added Amount of Methyl Ricinoleate

In order to optimize the added amount of methyl ricinoleate, we produced cultures to which we added after 24 hours either 0.83%, or 1.66%, or 10% (v/v) of methyl ricinoleate. The obtained results (Table 3) show that by adding 0.83% (v/v) of this ester, the highest γ-decalactone content is obtained in the aqueous phase and this without affecting the production of biomass.

TABLE 2

Influence of the amount of methyl ricinoleate (RM) added to cultures of 60 ml after 24 hours. Measurements were conducted after a culture period of 77 hours.

| Added amount of RM | 0 ml | 0.5 ml | 1 ml | 6 ml |
|---|---|---|---|---|
| OD at 620 nm | 8.74 | 8.00 | 7.94 | 8.98 |
| Lactone in mg/l | 1.02 | 32.22 | 27.24 | 18.78 |

Making use of the potential of *Sporobolomyces odorus* for bioconverting methyl ricinoleate into γ-decalactone, on non-supplemented distilling slops, is of interest, obviously. Indeed, by adding 1.66% (v/v) of this precursor, concentrations of the order of 45 mg/l of fragrant compound are obtained after a culture period of 144 hours, including 16.9 mg/l within 77 hours, which is a net improvement in production. Without adding this precursor, the yeast produced only 0.95 mg/l of fragrance after a culture period of 77 hours. This concentration amounted to 5.7 mg/l in presence of 1.66% (v/v) of exogenous castor oil.

Furthermore, it has been shown that γ-decalactone production increased with increasing additions of precursor. Actually, when RM addition was 0.83%, lactone concentration after a culture period of 77 hrs was 15.1 mg/l and 32.5 mg/l when precursor addition was 10.0%. The converse effect was observed on bioconversion yield, which decreases with the added amount of RM. This is due to an increase in the residual amount of RM.

6.1—Optimization of Methyl Ricinoleate Addition 6.1.1—Effect of an Early Addition of Precursor In the experiments performed above, addition of the precursor was carried out after a culture period of 24 hours. As a first step, the cells then had to adapt their metabolism to RM bioconversion.

An initial addition of RM was performed in order to determine whether an early presence of the precursor would enhance production by limiting this adaptation time.

TABLE 3

Influence of an early and fractionated RM addition on the growth of *S. odorus* and its production of γ-decalactone after a culture period of 77 hours.

| RM addition (% v/v) | Control 0.83% at t = 24 hrs | 0.06% at t = 0 hrs + 0.83% at t = 24 hrs |
|---|---|---|
| Biomass (OD at 620 nm) | 8.0 | 8.4 |
| [γ-decalactone] (mg/l) | 15.1 | 47.7 |

The obtained results, shown in Table 3, show that the addition of 0.06% (v/v) of RM at instant 0, followed by a second addition of 0.83% (v/v) 24 hours later, provided a significant improvement in lactone production as compared to the control. γ-decalactone concentration is multiplied by 3 after a culture period of 77 hrs.

6.1.2—Effect of a Fractionated Addition of Precursor

Subsequently to the above results, optimization of the system was undertaken by altering the added RM amounts on the one hand and the instants at which they were added to the culture medium, on the other hand.

In the conducted experiments, precursor additions were made at instants t=0, 24, 48 and 72 hrs. The obtained results are illustrated in FIG. 9. Their analysis showed that this fractionation did not alter the yeast's growth as compared to a control but considerably promoted the produced amounts of lactone. After 144 hrs, 142.7 mg/l were obtained instead of 44.7 mg/l when addition was completed in a single operation. Concentrations of 285 mg/l of fragrance after 216 hrs could be achieved with this strategy.

Moreover, with this RM addition process, we were able to minimize the required amounts of precursor and to increase the amount of γ-decalactone present in the aqueous phase.

6.1.3—Finding the Optimal Amounts of Precursor to be Added

With the aim of determining the concentration of RM with which a maximum concentration of γ-decalactone in the aqueous phase may be achieved, variable amounts of RM were added in fractions at instants t=0, 24, 48 and 72 hrs. The obtained results after a culture period of 96 hrs are shown in Table 4.

TABLE 4

Influence of the added RM amount on γ-decalactone production and bioconversion yield by *S. odorus*. The results shown were obtained after a culture period of 96 hrs. RM additions were made at t = 0, 24, 48 and 72 hrs.

| Amount of added precursor (% v/v) | 0.008 | 0.016 | 0.032 | 0.060 | 0.067 | 0.083 | 0.170 |
|---|---|---|---|---|---|---|---|
| Total addition (% v/v) | 0.033 | 0.066 | 0.132 | 0.240 | 0.268 | 0.322 | 0.680 |
| [γ-decalactone] (aq. phase mg/l) | 59.7 | 102.0 | 111.0 | 96.8 | 84.2 | 93.5 | 53.5 |
| Apparent bioconversion yield (% m/m)* | 19.5 | 17.5 | 9.1 | 4.4 | 3.5 | 3./1 | 0.8 |

$$* \frac{(\gamma\text{-decalactone mass}) \text{ aqueous phase}}{\text{added (RM mass)}} \times 100$$

Table 4 shows that:

apparent bioconversion yield is reduced in parallel with methyl ricinoleate content, amounts of produced lactone increase in parallel with the amount of exogenous methyl ricinoleate. Beyond 0.032% (v/v), γ-decalactone content is reduced.

These variations may be explained by:

lactone extraction from the culture medium is promoted by RM, a compound in which the lactone is more soluble than in the culture medium, RM transfer would be limited by the reduction in exchange surface due to its coalescence which increases with the added amount, the residual amount of RM increases with addition of RM, which lowers the observed bioconversion yield, a toxic effect from RM which increases with RM addition, a flaw within the composition of the distilling slops. Actually, lack of one oligo-element would be sufficient for blocking lactone synthesis.

The validity of these assumptions was checked and is the subject of the subsequent paragraphs.

6.1.4—Searching for Actual Bioconversion Potential of RM into a Lactone by *S. odorus*

In order to determine with which efficiency, *S. odorus* is capable of bioconverting RM into γ-decalactone, growth and production kinetics were obtained by adding limiting precursor amounts. Indeed, in these conditions, there is no residual RM at the end of the culture process, as shown by chromatographic analyses, so that the actual bioconversion yield may be determined. The obtained results are illustrated in FIG. 10. They show that the maximum obtained yield was 24%, whereas theoretical yield is 55%. Therefore it seems that the whole added RM is not exclusively used for γ-decalactone biosynthesis, but that it is also involved in other cell metabolisms.

At this point, it seems that:
- successive additions of RM are preferable to a single addition for producing γ-decalactone,
- RM addition at the beginning of the culture process is also favorable for producing lactone,
- the actual bioconversion yield of RM into lactone by *S. odorus* is 24% under the used culture conditions.

6.2—Is γ-Decalactone Toxic?

In order to determine whether γ-decalactone is toxic for cells, yeast growth kinetics on a distilling slop medium containing either 50 mg/l or 250 mg/l of lactone were obtained (FIG. 11). The dose of 50 mg/l of fragrant compound did not affect the yeast's growth for the first 50 hours of culture period. Beyond this point, a shift was observed. However, in the presence of 250 mg of lactone, the microorganism growth was significantly reduced. Indeed, the maximum achieved OD was 4 instead of 15 in the control. This same phenomenon was already observed by Ferron and al. (1996) who determined that the compatible dose with a non-zero cell growth rate is between 100 and 200 mg/l. This would partly explain why lactone concentrations of 250 to 300 mg/l were not exceeded under the retained experimental conditions.

6.3—Is RM Transfer Limiting

Growth and lactone production kinetics on a distilling slop medium were obtained by using a surfactant, Tween 20®, known for its dispersing properties. The latter was mixed with RM in one third-two thirds (v/v) proportions. The obtained solution was added in an amount of 0.09% (v/v) to the distilling slop medium at instants t=0, 24, 48 and 72 hrs.

FIGS. 12 and 13 illustrate biomass and γ-decalactone production, respectively. As for growth, the latter was not affected during the first 48 hours of culture period by the presence of Tween 20®. Beyond this point, a plateau was obtained while the cells continued to grow in the absence of the surfactant.

By comparing the lactone concentrations measured in the aqueous phase with and without Tween 20®, it is possible to demonstrate that the presence of this element increases the amount of fragrance present in this phase: 220 mg/l of γ-decalactone are measured after a culture period of 120 hrs in the presence of Tween 20®, and 135 mg/l in the control, which represents a 63% increase.

6.4—Does the Medium Composition have Deficiencies?

In order to check whether the blocking of γ-decalactone synthesis was not due to the absence of one or more oligo-elements, 96 hrs cultures were produced on the media which had been supplemented as follows:
- medium 0: distilling slops
- medium 1: distilling slops
  +−0.0 1 1 g/l of $FeSO_4$
  −0.13 g/l of $CaCl_2$
  −3 g/l of $MgSO_4$
- medium 2: distilling slops+1 g/lofyeast extract.

Methyl ricinoleate (4 times 0.06%) was added to these media at instants t=0, 24, 48 and 72 hrs.

The obtained results after a culture period of 96 hrs are summarized in Table 5. Examining them suggests that growth and lactone production are not basically altered by additions of salts and yeast extracts.

TABLE 5

Influence of supplementing the distilling slop medium, on the growth of *S. odorus* and its γ-decalactone production. The results shown were obtained after a culture period of 96 hrs.

| Medium | Medium 0 | Medium 1 | Medium 2 |
|---|---|---|---|
| Biomass (OD at 620 nm) | 15.8 | 12.1 | 14.8 |
| [γ-decalactone (mg/l) | 96.1 | 104.0 | 114.0 |

At this point, it seems that:
- distilling slop composition is not a factor capable of limiting γ-decalactone production
- the toxic effect of γ-decalactone, observed beyond 250 mg/l may be the cause of the limitation of its production by *S. odorus*.
- the positive effect of Tween 20® on the bioconversion reaction suggests that RM dispersion might enhance the amount of γ-decalactone present in the aqueous phase.

7—γ-Decalactone Production Example by *Sporobolomyces odorus* from Distilling Slops and Methyl Ricinoleate in a Fermenter

SUBSTRATE PREPARATION

After having dissolved the precipitated salts by heating and stirring, the solid particles contained in the. crude distilling slops are separated out by centrifugation. The pH of the distilling slops is-adjusted to 6 with 5 M NaOH and. an antifoam agent (Struktol®). is added in an amount of 0.01% (v/v).

STERILIZATION OF THE SUBSTRATE AND FERMENTER

The thus obtained substrate is introduced into the fermenter where it is sterilized at 120° C. for 20 minutes under 1.4 bars.

BATCH CULTURE

The fermenter is sown at an optical density of 0.2 (readout at 620 nm) from a pre-culture. Sterile methyl ricinoleate is added in an amount of 0.06% (v/v) at different instants after initiation of the culture, i.e. at instants t=0, 24, 48 and 72 hours. Temperature is controlled at 24° C., stirring at 500 rpm and ventilation at 0.4 VVM.

Alternatively, the culture may be produced continuously. Reaction parameters may vary according to the following exemplary indications:

| PARAMETER | INTERVAL | ADVANTAGEOUSLY |
|---|---|---|
| Temperature | 10–50° C. | 20–40° C. |
| Stirring | 50–1000 rpm | 100–700 rpm |
| Stirring | 0.10–10 VVM | 0.10–5 VVM |
| Ventilation | 0.01–20% (v/v) | 0.01–20% (v/v) |

C. In situ Extraction of γ-Decalactone 1.1—Selecting the Extraction System

A γ-decalactone concentration of 250 mg/l was never exceeded during its production without extracting this fragrant molecule, by *Sporobolomyces odorus* grown on distilling slops. This is related to the toxicity which this molecule exerts on yeast above 150 mg/l. In order to prevent the threshold concentration from being reached during the culture process, it must be extracted from the:aqueous phase as and when it is generated. Because γ-decalactone is lipophilic, its in situ extraction is possible with the use of hydrophobic substances.

The precursor used in the bio-synthesis of γ-decalactone, methyl ricinoleate (RM), which is also soluble in fat, is extracted in the same way as the produced natural fragrance. When the used extraction substance is an oil, an equilibrium is established between the aqueous and lipid phases. Considering RM consumption by cells in the aqueous phase, a transfer of the precursor occurs from the lipid phase to the aqueous phase.

The following investigations were primarily carried out by using hydrogenated coconut oil (HNCH) and at certain times, using TTT as a solid fat for extracting γ-decalactone in situ.

1.2—Study of the Dose of Precursor to be Added in the Case of Cultures Produced in Presence of HNCH As RM is a lipid, it is also solubilized in HNCH. The amount of precursor present in the aqueous phase then depends on its partition coefficient between both phases. Because this parameter is largely in favour of the lipid phase, only a small amount of the added RM remains in the aqueous phase and is therefore available to the cells. It is also likely that the precursor becomes a limiting factor in the synthesis of γ-decalactone, and this all the more as the cells are no longer submitted to the toxicity of this molecule. Four cultures were produced, receiving respectively:

4×0.03% (v/v) of RM
4×0.06% (v/v) of RM (control)
4×0.12% (v/v) of RM
4×0.18% (v/v) of RM Additions of RM were performed at instants t=0, 24, 48 and 72 hours. These cultures were produced in 250 ml erlenmeyers containing 5 g of HNCH and 60 ml of sown distilling slops at an initial yeast cell density of 0.2 units of $OD_{620}$ (optical density measured at 620 nm).

The obtained results (FIG. 14) show that yeast growth kinetics are identical, RM additions are 4×0.03, 0.06 or 0.12% (v/v). Furthermore, growth rate is substantially the same for all the tests during the first 75 hours of the culture process. On the other hand, an addition of 4×0.18% (v/v) of precursor clearly improves growth of S. odorus. After a culture period of 150 hours, $OD_{620}$ reaches a value of 15 versus only 8 in the other cases.

As for γ-decalactone production (Table I), it increases with the dose of added precursor and reaches 980 mg/l after a culture period of 312 hours with an addition of 4×0.18% (v/v). This lactone concentration largely exceeds that of 250 mg/l obtained earlier in the absence of HNCH.

TABLE I

γ-decalactone production by S. odorus versus the amount of added RM and in the presence of HNCH (5 g/vial). These measurements were conducted after a culture period of 312 hours.

| Added amount of RM | 4 × 0.03% | 4 × 0.006% | 4 × 0.12% | 4 × 0.18% |
|---|---|---|---|---|
| γ-decalactone (mg/l) | 147 | 265 | 370 | 980 |

The solid fat used (hydrogenated coconut oil) therefore proved to be a good system for extracting γ-decalactone. By multiplying the dose of added RM by 3, the concentration of 250 mg/l obtained for cultures produced in the absence of this "extraction fat" could be increased by a factor 4.

1.3—Influence of an Addition of Tween 20® or Struktol® in the Presence of HNCH

After having noticed the absorption of methyl ricinoleate in the extraction fat during the chromatographic dosage of γ-decalactone, it seemed interesting for us to try and limit this phenomenon by adding additives, such as a surfactant at a concentration which respects cellular integrity, Tween 20® or an antifoam agent Struktol® which may also act as solubilization vector.

The following experiences were conducted:

4 additions of 0.18% (v/v) of RM,
4 additions of 0.18% (v/v) of RM+0.01% (v/v) of Struktol®,
4 additions of 0.18% (v/v) of RM+0.01% (v/v) of Tween 20®.

RM was added (by itself or mixed with the additives) at instants t=0, 24, 48 and 72 hours.

With the aim of increasing the productivity of the system by implementing an in situ extraction of γ-decalactone, two series of tests were conducted; one at an initial cell density of 0.2 (control), the other at an initial cell density of 4.

TABLE II

Influence of an addition of Tween 20 ® [0.01% (v/v)] or Struktol ® [0.01% (v/v)] while growing S. odorus in the presence of HNCH (5 g/vial) at initial cell densities of 0.2 and 4. Evaluation of biomass and γ-decalactone production was performed after a culture period of 312 hours.

| Initial biomass (OD at 620 nm) | Parameters | Culture conditions | | |
|---|---|---|---|---|
| | | control | Struktol ® | Tween 20 ® |
| 0.2 | Final biomass | 17.54 | 9.87 | 9.43 |
| | Total γ-decalactone production (mg/l) | 810 | 1400 | 1180 |
| 4 | Final biomass | 21.37 | 11.97 | 15.38 |
| | Total γ-decalactone production (mg/l) | 1110 | 990 | 1530 |

The obtained results (Table II) show that, whatever the initial sowing density, adding the additives reduces the cell concentration reached after a culture period of 312 hours.

As for total lactone production (Table II), it is enhanced by the presence of Struktol® and to a lesser extent by addition of Tween 20® when the initial cell density is 0.2. The influence of these additives on total γ-decalactone production differs in tests performed with a cell sowing density of 4. Indeed, in the latter case, lactone concentration obtained in presence of Struktol® (990 mg/l) is less than that of the control (1111 mg/l). Only Tween 20® enables an increase of the amount of produced lactone in both cases.

Therefore, it seems that the conditions which provide the best total yield in the production of γ-decalactone, are the following: Initial cell density of 4, Additions at instants t=0, 24, 48 and 72 hours of 0.18% (v/v) of RM+0.01% (v/v) of Tween 20®.

1.4—Influence of Extra Additions of Precursor

In order to check whether the availability of the precursor in the aqueous phase is actually the factor which limits lactone synthesis beyond 150 hours, a culture with an initial cell density of 4 is initiated. After inoculation, the suspension receives additions of 0.18% (v/v) of RM
0.01% (v/v) of Tween 20® and
0.01% (v/v) of Struktol®.

These additions are performed at instants t=0, 24 48, 72, 144 and 168 hours. These additives are used with the aim of limiting foam production during the culture process on the one hand (Struktol®) and on the other hand for optimizing transfer of the precursor to the cells through the cell membranes (Tween 20®).

The obtained results (FIG. 15) show that whereas biomass growth is not affected by both extra additions of RM, this is not the case for γ-decalactone productivity. The latter is 5.3 mg/l/h during the first 150 hours of culture, then it resumes with a rate of 19 mg/l/h as a result of fresh additions of precursor and it continues until t=216 hours. Total productivity over a culture period of 240 hours is then 6.66 mg/l/h. Accordingly, the hypothesis put forward earlier is thus verified: transfer of RM in the lipid phase to the aqueous phase becomes a limiting factor for producing lactone beyond 150 hours. Finally, by a fresh addition of RM and of additives after 144 hours, γ-decalactone production is reinitiated with an approximately 4-fold rate. At this stage, it seems that by adding together RM, Tween 20® and Struktol®, a total productivity of 5.3 mg/l/h may be achieved during the first 150 hours: of the culture process. Availability of RM in the aqueous phase is a rapidly limiting factor to the production of lactone. One of the solutions to this problem might consist in a spatial separation of the RM conversion and lactone extraction steps.

1.5. γ-Decalactone Production Kinetics in the Presence of TTT

In addition to hydrogenated coconut oil, the mixture of TTT vegetable fats was tested as a system for extracting γ-decalactone in situ. For this purpose, 0.18% (v/v) of RM, 0.01% (v/v) of Tween 20® and of 0.01 (v/v) of Struktol® is added to a culture with an initial cell density of 4, provided with TTT (5 g/vial). These additions are performed at instants t=0, 42, 48, 72, 144 and 168 hours. After sterilization at 120° C. for 20 min, of the TTT mixture (5 g) contained in a 250 ml erlenmeyer, the latter is freshly melted by heating and spread over the internal surface of the erlenmeyer up to a height of 5 cm (measured from the bottom) by having it rotate around its vertical axis inclined by about 45° C. Once the fat is solidified, 60 ml of distilling slops, having been sterilized and cooled off beforehand, are introduced into the erlenmeyer. Sowing is effected after having added RM, Tween 20® and Struktol®. The obtained results (FIG. 16) show that the yeasts stop growing after a culture period of 72 hours; beyond this point, a plateau is established around a biomass value substantially equal to 11. As for γ-decalactone, its production rate is 6 mg/l/h during the growing phase. It then continues to increase and subsequently maintains a constant value of 7.8 mg/l/h.

BIBLIOGRAPHY

Lee S. J., Lin S. J. and Chou C. C.: "Growth of and production of γ-decalactone by *Sporobolomyces odorus* in jar fermentor as affected by pH, aeration and fedbatch technique", *Journal of fermentation and bioengineering*, 82(1), 195–199 (1995).

Feron G., Dufossé L., Pierrard E., Bonnarme P., Le Quere J. L., Spinnler H. E.: "Production, identification, and toxicity of γ-decalactone and 4-hydroxydecanoic acid from Sporidiobolus spp", *Applied and environmental microbiology*, 62(8), 2826–2831 (1996).

Jourdain N., Goli T., Jallajeas J. C.: Aroma components production by immobilized cells. *In Topic and flavour research*, Eds Berger R. G., Nitz S., Shreier P., 1–2 April, München, D, 427–441 (1985).

Gallois A., Gross B., Langlois D.: *Influence of culture conditions on production of flavour compounds by 29 lignolytic Basidiomyucetes. Mycol. Res.*, 94 (4), 494–504 (1990).

Dufossé L. H. et al: Strategies to overcome toxicity during flavour production by microorganisms: the case of γ-decalactone from *Sporidiobolus salmonicolor*. International *Symposium on Flavours and Sensory Related Aspects Mar.* 6–7, 1997.

What is claimed is:

1. A process for preparing volatile fragrant aromatic compounds comprising the steps of:
   (a) growing under fermentation conditions in an aqueous phase medium, at least one microorganism which produces said aromatic compounds in the presence of a substrate comprising a distilling hups residue obtained from distillation of fermentation products from parts of plants,
   (b) bringing the medium formed in step a) into contact with a solid lipid phase medium at room temperature,
   (c) recovering by absorption in the lipid phase medium the volatile fragrant aromatic compounds.

2. The process according to claim 1, wherein the substrate is a distilling hups residue from wine distillation.

3. The process according to claim 1, wherein the plants are selected from the group consisting of beet, sugar cane, malt, barley, and wheat.

4. The process according to claim 1, wherein the substrate comprises a distilling hups residue from wine distillation and the lipid phase medium comprises vegetable fat or a mixture of vegetable fats.

5. The process according to claim 1, wherein the microorganism is selected among the group consisting of a bacterium, a yeast or a fungus.

6. The process according to claim 1, wherein the growing step is carried out in the presence of a precursor promoting the synthesis of the volatile fragrant aromatic compounds.

7. The process according to claim 1, wherein the growing step is carried out in the presence of ricinoleic acid or a derivative of ricinoleic acid assimilable by the microorganism(s).

8. The process according to claim 1, wherein the growing step is carried out in the presence of an ester of ricinoleic acid.

9. The process according to claim 1, wherein an amount of methyl ricinoleate is applied during the growing step so that an amount of γ-decalactone is produced between 50 mg/l and 700 mg/l in the aqueous phase.

10. The process according to claim 1, wherein the growing step is carried out for a minimum period of time of 24 hours.

11. The process according to claim 1, wherein initial optical density (OD) at 620 nm of the added microorganisms for carrying out the growing step is between 0.1 and 20.

12. The process according to claim 8, wherein initial optical density (OD) at 620 nm of the added microorganisms for carrying out the growing step is between 5 and 15.

13. The process according to claim 1, wherein the culture medium comprises a surfactant.

14. The process according to claim 1, wherein the microorganisms are selected among the following wild-type or genetically modified microorganisms:

*Sporobolomyces odorus, Yarrowia lipolytica, Saccharomyces cerevisiae, Lenzites betulina,* Penicillium sp., Fusarium sp., *Fusarium moniliforme, Cylindrocarpon*

*radicicola, Lactococcus lactis, Bacillus, Aspergillus, Claviceps purpurea, Streptomyces dimorphogenes.*

15. The process according to claim 1, wherein the lipid phase medium comprises a hydrogenated coconut oil or a mixture of tripahnitine (40%), tristearine (20%) and triolein (20%) (TTT type).

16. The process according to claim 1, further comprising a step for separation of the absorbed aromatic compounds in the lipid phase medium by extraction with an alcohol.

17. The process according to claim 16, wherein said extraction with an alcohol comprises the steps of:
   1) solubilizing the solid lipid medium in 96° ethanol in a volume ratio of 1:10,
   2) churning of the ethanol solution at −20° C. for an hour,
   3) separating the aromatic compounds containing alcohol from the crystallized lipid medium.

18. The process according to claim 1, wherein said parts of plants comprise plant organs.

19. The process according to claim 7, wherein the derivative of ricinoleic acid is a salt of ricinoleic acid.

20. The process according to claim 8, wherein the ester of ricinoleic acid is methyl ricinoleate.

21. The process according to claim 11, wherein initial optical density (OD) at 620 nm of the added microorganisms for carrying out the growing step is between 0.2 and 15.

22. The process according to claim 11, wherein initial optical density (OD) at 620 nm of the added microorganisms for carrying out the growing step is between 1 and 15.

23. The process according to claim 12, wherein initial optical density (OD) at 620 nm of the added microorganisms for carrying out the growing step is between 5 and 10.

24. The process according to claim 17, wherein the step of: separating the aromatic compounds containing alcohol from the crystallized lipid medium is carried out by filtration.

* * * * *

UNITED STATES PATENT AND TRADEMARK OFFICE
CERTIFICATE OF CORRECTION

PATENT NO.    : 6,518,050 B1                                              Page 1 of 1
DATED         : February 11, 2003
INVENTOR(S)   : Christian Ambid et al.

It is certified that error appears in the above-identified patent and that said Letters Patent is hereby corrected as shown below:

Column 22,
Lines 18, 26 and 31, delete "hups" and replace with -- slops --.

Column 23,
Line 17, delete "tripahnitine" and replace with -- tripalmitine --.

Signed and Sealed this

Second Day of December, 2003

JAMES E. ROGAN
*Director of the United States Patent and Trademark Office*